United States Patent [19]

Le Febre et al.

[11] Patent Number: 5,552,042
[45] Date of Patent: Sep. 3, 1996

[54] RIGID SILICA CAPILLARY ASSEMBLY

[75] Inventors: David A. Le Febre, Camino; James R. Lansbarkis, El Dorado; Roy V. Semerdjian, Fair Oaks, all of Calif.

[73] Assignee: UOP, Des Plaines, Ill.

[21] Appl. No.: 394,127

[22] Filed: Feb. 24, 1995

[51] Int. Cl.⁶ .................................................. B01D 15/08
[52] U.S. Cl. ........................................ 210/198.2; 96/101
[58] Field of Search ................................ 95/87; 96/101, 96/102; 210/198.2, 656

[56] References Cited

U.S. PATENT DOCUMENTS

| | | | |
|---|---|---|---|
| 3,122,014 | 2/1964 | Dobbins | 96/101 |
| 3,143,404 | 4/1964 | Heigl | 96/101 |
| 3,182,394 | 5/1965 | Jentzch | 96/101 |
| 3,389,538 | 6/1968 | Carel | 96/102 |
| 3,514,925 | 6/1970 | Bossart | 96/101 |
| 3,531,919 | 10/1970 | Keulemans | 96/101 |
| 3,808,125 | 4/1974 | Good | 96/101 |
| 4,038,055 | 7/1977 | Varano | 96/102 |
| 4,293,415 | 10/1981 | Bente | 96/101 |
| 4,483,773 | 11/1984 | Yang | 96/101 |
| 4,509,964 | 4/1985 | Hubball | 96/101 |
| 4,966,785 | 10/1990 | Springston | 96/101 |
| 5,114,439 | 5/1992 | Yost | 96/102 |

*Primary Examiner*—Ernest G. Therkorn
*Attorney, Agent, or Firm*—Thomas K. McBride; Eugene I. Snyder

[57] ABSTRACT

A new type of tubular assembly especially adaptable to capillary columns for use in gas chromatography, comprises a capillary wound on and fused to a hollow mandrel and stress relieved by heating. The entire assembly is rigid and is more resistant to fractures than prior available columns. Variants include rigid assemblies integral with heating means. Solid, brittle stationary phases can be readily accommodated in these assemblies because of their rigidity and structural strength.

21 Claims, 1 Drawing Sheet

RIGID SILICA CAPILLARY ASSEMBLY

FIELD OF THE INVENTION

This invention relates to a capillary assembly especially useful in gas liquid and gas solid partition chromatography. In particular, the invention relates to a rigid, relatively stress-free capillary assembly of fused silica. The assembly which is the subject of our invention is used in the preparation of coated columns whose temperature limitations far exceed those of prior art materials, which permit fabrication of columns with a much greater inherent lifetime and physical stability, and which promise to make possible the fabrication of columns heretofore unknown or difficult to prepare at best.

Although glass capillary and open tubular columns had been used in gas chromatography for some time, their usefulness was limited by their fragility and chemical reactivity. Columns generally were used as helical coils which were inflexible, therefore susceptible to stress fracture, and because of surface hydroxyls characteristically present on glass surfaces the peak shapes of reactive materials such as phenols, amines, and mercaptans inter alia tended to be distorted even when the glass surface was deactivated. Thus, in the "early" gas chromatographic days of capillary and open tubular columns the many advantages of glass capillary and open tubular columns were accompanied by serious disadvantages.

In about 1980 the situation changed remarkably based on art taught by U.S. Pat. No. 4,293,415. The patentee recognized that silica capillary columns for gas chromatography could be made in much the same manner as hollow optical fibers, e.g., liquid core quartz fibers. The impetus for using the silica, rather than a borosilicate glass, in capillary and/or open tubular columns is associated with the lower reactivity of the silica surface. However, the non-annealed silica tube needed a protective coating on the outside surface, such as a polyiimide coating, to prevent additional stress arising from abrasion and the adsorption of moisture. Since the capillaries of the patentee were not stress relieved, as by annealing, they were quite susceptible to stress fractures, and protective coatings were an indispensable prerequisite to prevent microfractures due to additional stress. In this manner columns more flexible than glass could be prepared. After treatment of the silica surface with deactivating agents the same as, or analogous to, those used for glass columns, more symmetrical peaks were obtained in gas chromatography and the patentee's silica columns even could be used for classes of compounds for which glass columns were unsatisfactory, as for example phenols, volatile carboxylic acids, mercaptans, and aliphatic amines. It is important to realize that the patentee's columns were not annealed in order to preserve flexibility.

The foregoing state of affairs presents a conundrum. If the capillary or tubing was not annealed it remained flexible (a desirable property) but under stress leading to fracture susceptibility. Therefore, a coating was required to protect against stress fractures arising from surface scratches, water adsorption, and so on. But the coating imposes temperature limitations, since most coatings are organic, as well as lifetime limitations arising from poor coating adhesion. If the capillary is annealed stress is relieved but the structure is no longer flexible and is then subject to fracture upon flexure. There are no practical means of retaining the preferred and desirable helical coil shape without subjecting the coil to flexure in normal use. On the other hand, inflexibility, or rigidity, is desired for using certain inorganic stationary phases which themselves are quite brittle and subject to stress damage.

Our invention presents a solution to the foregoing conundrum. Our invention provides a silica capillary or open tubular assembly wound on and fused to a mandrel, with the entire assembly being annealed so as to present a relatively stress free, rigid winding. Because of the relative lack of stress no external surface coating is needed. Therefore the temperature and lifetime limitations associated with such coatings are obviated. Because of the rigidity of the assembly brittle coatings, especially of inorganic materials, may be deposited within the capillary or tubes as a stationary phase and usefully employed over extended time periods. As will also become apparent from the ensuing description of the preparation of our assembly, such assemblies may be made in a plethora of coil diameters, coil pitch, and tubular inside diameters. Thus our invention not only overcomes the limitations of the prior art but also extends the applicability of capillary and tubular columns into parts of the working universe not previously accessible or believed possible.

SUMMARY OF THE INVENTION

The purpose of this invention is the preparation of a relatively stress free, rigid capillary or open tubular assembly not requiring a protective coating while stable to operation at high temperature, and stable to repeated temperature cycling for long periods of time. One embodiment is a helical coil of a hollow silica tube wound on the outside of a hollow mandrel of a material of similar coefficient of expansion. The coils are in contact with the mandrel along substantially the entire length of the coils and are fused to the mandrel at substantially all contact points. In a more specific embodiment the mandrel is silica. In yet another embodiment the mandrel has a diameter between about 3 and about 10 inches. In still another specific embodiment the inside diameter of the tubular coil ranges from about 50 microns up to about 5 mm. Other embodiments will be apparent from the following description.

DESCRIPTION OF THE INVENTION

Figure 1:
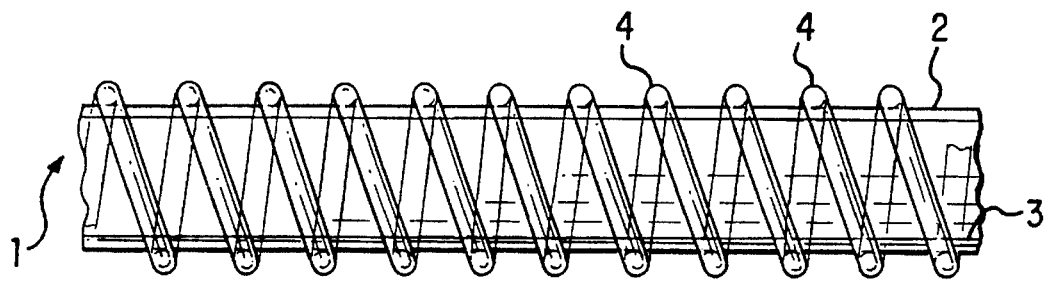
FIG. 1 is a plan view of the rigid assembly.

Capillary and open tubular columns are commonly employed in gas chromatography. Where the capillary is not annealed the assembly is under stress, making it susceptible to fracture and requiring that the outside surface be coated with a protective material which itself limits the column lifetime because of adhesion limitations and circumscribes operational parameters because of temperature limitations. If the stress is relieved the structure is no longer flexible and becomes susceptible to flexural fractures. However, to date there are no means of rigidly retaining and supporting the helical forms of columns so commonly used, so that in prior art practice helically wound columns always are subject to flexing and fracture. Our invention is a solution to this problem. Our solution is elegant, simple, and extraordinarily effective. Our solution is a rigid assembly of a helical coil of a capillary or open tubular column wound on a mandrel of a material with a similar coefficient of expansion. The coil is in contact with the outside of the mandrel throughout the length of the coil and is fused to the mandrel at all, or virtually all, contact points.

We use "mandrel" in its usual dictionary meaning, i.e., a core around which other material may be bent or otherwise shaped. The mandrel of our invention has a diameter of several inches and also is several inches long. More specifically, a mandrel diameter is most often in the range between about 3 and about 10 inches, with a preferred diameter between about 5 and about 7 inches. However, it is to be stressed that the foregoing diameters represent practical limitations arising largely from the chromatographic instruments presently commercially available and do not represent limitations pertaining to operability. The length of mandrel is sufficient to support the length of capillary or open tubular column wound around it but otherwise is not at all critical nor an element of our invention. In the practice of our invention lengths between about 3 and 10 inches are most often are used in the preparation of our rigid assemblies. The mandrel is generally hollow, although in principal a solid core mandrel also may be used in the practice of our invention. However, a hollow mandrel is preferred for ease of construction, since it will require less heat in the preparation of the rigid assembly which is our invention and also lead to lower dimensional changes along the diameter. Generally a wall thickness of about 1.5 up to about 3 mm will suffice to provide the necessary stiffness. To insure the structural rigidity of the assembly the diameter of the mandrel needs to be about three times the diameter of the capillary or other open tubular column wound on the mandrel.

The mandrel is a substantially linear segment of material which has a coefficient of expansion similar to the helical coils wound on the outside of the mandrel. Such materials include quartz (to be understood as a high purity, amorphous, silica glass) and other forms of silica. As a general rule one desires that the material of construction of the mandrel have a coefficient of thermal expansion which is within 10% of that of the wound capillary or open tube wound on the mandrel over the temperature range contemplated for use of the assembly, which for the purpose of this application can be taken as the range from about $-100°$ up to about $800°$ C. Some form of silica is the preferred material for the mandrel.

A capillary or open tubular column is wound on the outside of the mandrel in a continuous helical fashion. The preferred material for the helical winding is silica, and fused silica in particular, with quartz an especially preferred material. The hollow coils may have an inside diameter as little as about 50 microns and as great as about 5 mm. Using a fused silica capillary to exemplify our invention, the fused silica capillary is wrapped directly on the mandrel while the mandrel is heated from its inner surface. Where the mandrel also is fused silica, it can be heated to just below its softening temperature of approximately $1550°$ C. causing the capillary to fuse onto the mandrel at the tangent of the capillary to the mandrel. The point of fusion is only several microns wide and does not visually distort the shape of the capillary. Fusion of the capillary to the mandrel affords great rigidity and structural stability to the coils, especially where fusion is effected along substantially the entire length of the coiled winding. As the mandrel rotates, the capillary is cross-fed across the mandrel to form windings that are adjacent to each other on the mandrel. By varying the mandrel cross-feed the adjacent capillaries can be made to touch each other such that each capillary winding could be in contact with both the mandrel and each of its adjacent capillary neighbors. To make connections to the termini of the helical coils, the beginning and ending winding on the mandrel is spaced at a higher pitch from the body of the windings resulting in the ends of the windings being spaced apart from the body of the windings and generally adjacent to the edges of the termini of the mandrel. To further increase rigidity, the adjacent capillaries in contact also could be fused to each other at a multiplicity of contact points. To relieve stress and afford a relatively stress-free rigid assembly the entire assembly can be heated at a temperature appropriate to the materials of construction. Although one might believe that the annealing temperature of the material would be the most appropriate one for heat treatment we have found this is not the case for fused silica. Although the annealing temperature of fused silica is in the range of $1120°$–$1118°$ C. heat treatment within this temperature range, at least for reasonable times, appears inadequate to produce a mechanically stable structure sufficiently stress-resistant to be stable under the normal handling and thermal cycling conditions. Instead we have found it preferable to heat the assembly to a temperature of about $1500°$ C. We note that the softening temperature of fused silica is about $1600°$ C., and heating to such temperatures must be avoided.

The foregoing description was that for a helical capillary winding, but it is apparent that the description is equally valid for any open tubular winding. Another embodiment can be readily envisioned where a helical preformed coil is placed within the annular space of a hollow mandrel with the coil in contact with the inner surface of the hollow mandrel along a substantial portion of the coil length. The mandrel then can be heated on the outside and fused contact be made with the helical coil on the inside of the mandrel along either substantially the entire length of the coil or only a portion of the coil length.

It is necessary to connect the termini of the capillary or open tubular helical coils to GC instrument conduits when our rigid assembly is used as a GC column. Although many methods and procedures for making such connections are possible, we describe here just one such approach as illustrative rather than limiting. The description is rather detailed to aid in understanding, but we emphasize its illustrative, non-limiting aspects.

Connections to the coils may be made through tapered thick wall fused silica tubing (original I.D. 1 mm and original O.D. 3 mm and <3 inches long), which interfaces a capillary (0.2–0.6 mm outside diameter) at the small end of its taper, and at the opposite end provides an I.D. tapered interface for metal tubing or coated fused silica capillaries, which allow connection to the GC inlet and detector GC ports. The connectors can be made by drawing down a cylindrical tube which has been ground down approximately ½ to ¾ mm longitudinally for its entire length forming a flat surface and then drawn into a taper for about ⅓ to ½ of its length such that the tapered end's inside diameter is slightly larger than the outside diameter of the capillary.

The tapered tubing is then radiused along its ground length, e.g., using an oxygen hydrogen torch, to generate a radius which duplicates the mandrel radius, such that the ground section of the tapered tube fits exactly with the radius of the mandrel. This process is accomplished at a temperature low enough as to not deform the ground section. The small tapered end of the ground surface is further ground (tube wall removed) to break through the wall of the tapered tubing to form an opening (triangular slot in the plane of the ground surface). This triangular slot accommodates the line contact (fused bond) between the mandrel and the end of the wound capillary such that there is a slight overlap between the end of the capillary and the small end of the tapered connector. Once the tapered connector is in place, the connector is fused to the mandrel by heating the inside of the mandrel in the vicinity of the connector. Where the small end of the fused silica connector overlaps the end of the capillary which is also fused on the mandrel, a cement such as silica sol with a filler is used to seal the slight annular void between them.

When both connectors have been attached, the assembly consisting of the two connectors, the mandrel and the wound capillary tubing is placed in an oven and heated to 300° C. and cured for several hours (to cure the cement) then brought up to approximately 1550° C. in a refractory oven and annealed for 4 to 8 hours.

Figure 2:
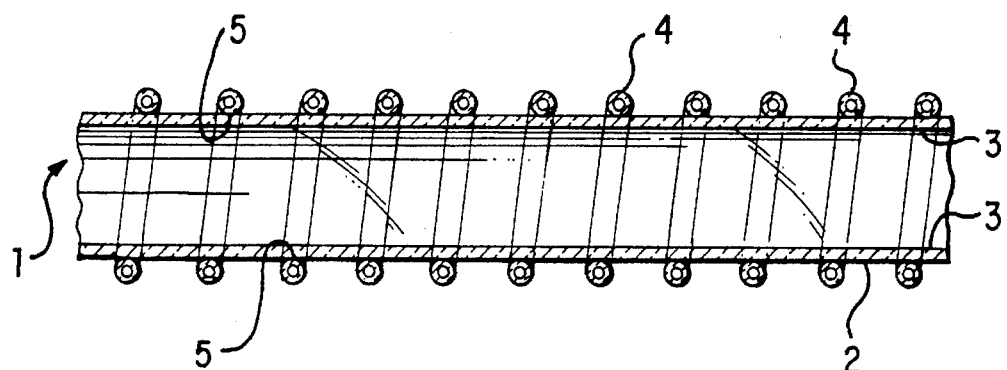
FIG. 2 shows an axial cross section of the rigid assembly of our invention.
Figure 3:
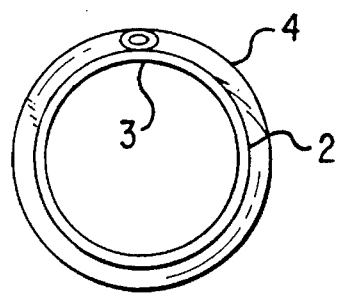
FIG. 3 is a transverse section of the rigid assembly of our invention.
Figure 4:
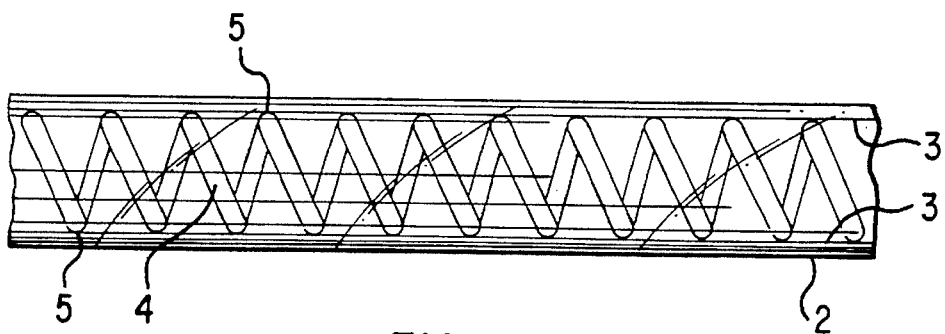
FIG. 4 shows an alternate embodiment of the rigid assembly of our invention with the helical coils on the inside of the tubular mandrel.

Our invention also may be understood with the aid of the figures. FIG. 1 is a plan view of the rigid assembly, showing the mandrel 1 as a hollow tube with an outside surface 2 and an inside surface 3. The annular space is of course bounded by the inside surfaces 3. Helical coils of hollow tubing are wound on the outside surface 2 of the mandrel. At the points of contact 5 between the coils and the outside surface (see FIG. 2) the tubing is fused to the mandrel. Since the contact width is very small in relation to the diameter of the tubing such fusion introduces virtually no deformation of the generally tubular shape of the coils. As both FIGS. 1 and 2 clearly show, the hollow tube wound on the outside surface of the mandrel affords a continuous, helical coil with a multiplicity of windings. FIG. 3 depicts a section transverse to the mandrel, i.e., along its diameter, and clearly shows the coils are in fused contact with the outside surface i of the mandrel along substantially the entire length of the coil. FIG. 4 represents the variant where the coil is placed within the annular space of a hollow mandrel and in contact with the inside surface 3 of the mandrel, in contrast to the case where the coil is wound on the mandrel's outside surface. However, other than the relative location of the helical wound coils relative to the two surfaces of the mandrel the embodiments are strictly analogous.

Another important variant of our invention is one where a heating element is integral to the mandrel, so that the entire assembly is self-heating. The reference of a heating assembly integral to the mandrel is not meant to imply that the heating element is structurally inseparable from the mandrel, although this certainly is an acceptable embodiment. Rather what is meant is that the heating element and rigid assembly constitute, or are capable of forming, a unit incorporating heating means. At one extreme this variant of our invention arises by deposition of a thin metallic film on the mandrel surface other than that upon which the capillary or open tubular column is helically wound. That is, if the capillary be wound on the outside surface, then the heating means is on the inside surface, and vice versa. The thin film is not a continuous film, but rather is a continuous, discrete strip in the form of, e.g., a helical pattern, a series of linear strips running lengthwise along the mandrel and more-or-less uniformly spaced along the circumference, and any other of the infinite number of patterns which would lead to uniform heating of the mandrel surface on which the film is deposited.

In another embodiment the heating means may be incorporated into the rigid assembly without being a structural part of the assembly. For example, where the capillary or open tubular column is wound on the outside surface of the mandrel a resistance wire may be wound in contact with, but not firmly affixed to, the inside surface of the mandrel. Another example is a metallic resistance element spirally wound, and the spirals helically wound on the inside surface of the mandrel. It is clear that in this embodiment the heating means is detachable and separable from the rigid assembly, thus capable of independent replacement in case of damage, or of reuse with a multitude of interchangeable rigid assemblies. Again, there are an infinite number of heating means separable from the rigid assembly itself yet come within the scope of a heating means integral to the rigid assembly of our invention.

A reason for incorporating heating means into the rigid assembly of our invention is that the resulting unit permits greater flexibility and control of the helically wound capillary or hollow tube wound on the mandrel. Thus, heat is generated in close proximity to the capillary winding and is quickly passed from the mandrel surface being heated directly to the windings. This makes it possible to achieve higher heating rates, which sometime is advantageous in desorbing materials from stationary phases where there is a high heat of desorption and where the tendency of tailing during desorption is decreased by a high heating rate. A high heating rate also permits one to achieve high bakeout temperatures more rapidly. That is, there is a tendency for some materials to be incompletely desorbed from a stationary phase, with residual adsorbed material being desorbed in subsequent uses of the column. Especially where the stationary phase is non-organic, high bakeout temperatures between analyses ensures complete desorption and elimination of memory effects.

As is clear from our introductory remarks, the rigid assembly of our invention represents a significant advancement in the design and fabrication of gas chromatographic columns. As is well known from the prior art, a multitude of organic materials can serve as the stationary phase, all of which may be used in the practice of our invention. As is also well known in the prior art the silica surface may need to be treated prior to its being coated with an organic stationary phase in order to deactivate the silica surface, although the high temperature treatment of our rigid assemblies prior to use itself serves as a deactivating procedure. However, an important characteristic of our rigid assemblies is that they are well-suited for the preparation of gas chromatographic columns where the stationary phase is an inorganic solid which usually is brittle and inflexible; vide infra. An example is provided within.

From the foregoing description it will be apparent that many specific variants of our invention will occur to the skilled worker, all of which are intended to be subsumed by and within the scope of our claims. The following merely illustrate our invention by describing illustrative examples in detail, and are clearly to be understood as representational of some aspects of our invention rather than being limitations.

Preparation of Chromatographic Column with Solid Stationary Phase; Use in Analysis.

A volume of approximately 800 μL of sodium aluminate (50 g 1.0 N KCl solution in water/1.3 g Alcoa Sodalum 200) was introduced into a 320 μm id column (~31 m in length) and was pushed through the column using helium at a pressure of ~30 psig and ~50 mls/min. This left a thin coating of sodium aluminate in the column. Varying the flowrate and pressure will vary the coating thickness. Also, varying the concentration of sodium aluminate will affect the coating thickness. The column was then slowly heated to 225° C. with a helium gas purge (~20 mls/min) to remove the remaining water. The column was then slowly heated to 500° C. (2° C./min) to calcine the phase.

The phase also can be introduced by using multiple small injections instead of one large injection. The methodology followed is known as dynamic coating. The phase may also be introduced by completely filling the column with the phase solution and slowly evaporating the water. This technique is known as static coating.

The column was installed into the gas chromatograph (GC) and heated to 350° C. for 2 hrs with a head pressure of 15 psi to sweep away any contaminants that may be present in the column. The column temperature then was set to a temperature of 50° C. and the velocity of the carrier gas was set to ~20 $cm^3$/sec. A 1 µL injection of ASTM-110 standard (diluted 50% in pentane) was injected into the injection port of the GC using a 10 µL syringe. A split ratio of ~300:1 was used to control the amount of sample that entered the column. After 1.5 minutes, the GC ramped the temperature to 250° C. using a ramp rate of 25° C. per minute. The GC then held the temperature constant for 15 min. Separation of most of the components of this C6–C44 n-alkane blend was obtained under these non-optimized conditions.

In another analysis the column temperature was set to a temperature of 35° C. and the velocity of the carder gas was set to ~20 $cm^3$/sec. A 1 µL of ASTM-100 standard was injected into the injection port of the GC using a 10 µL syringe. A split ratio of ~300:1 was used to control the amount of sample that entered the column. After 3 minutes, the GC ramped the temperature to 250° C. using a ramp rate of 25° C. per minute. The GC then held the temperature constant for 15 min. Partial separation of the components of this C5–C15 alkane blend was readily achieved under these non-optimized conditions.

The column temperature was set to a temperature of 75° C. and the gas carrier flow rate set to $cm^3$/sec. A 1 µL injection of 50% methyl-t-butyl ether/50% mesitylene was injected into the injection port of the GC using a 10 µL syringe. A split ratio of ~300:1 was used to control the amount of sample that entered the column. After 3 minutes, the GC ramped the temperature to 350° C. using a ramp rate of 25° C. per minute. The GC then held the temperature constant for 15 min.

What is claimed is:

1. A rigid assembly of a hollow silica tube helically wound on a silica mandrel comprising:
   a. a mandrel of a substantially linear segment of a first hollow silica tubing, said mandrel having an inside surface within said tubing and an outside surface;
   b. a helical continuous coil length of a second hollow silica tube located on the outside surface of said mandrel and in fused contact with said outside surface at a multiplicity of points along the length of said helical coil;
   c. each portion of said coil having a direction generally transverse to the linear segment of said mandrel.

2. The rigid assembly of claim 1 where the mandrel has an outside diameter between about 3 and about 10 inches.

3. The rigid assembly of claim 1 where the continuous tubular coil has an inside diameter between about 0.05 and about 5 mm.

4. The rigid assembly of claim 1 further characterized by having a multiplicity of adjacent coils in fused contact with each other.

5. A rigid assembly of a hollow silica tube helically wound within the annular space of a hollow silica mandrel comprising:
   a. a mandrel of a substantially linear segment of a first hollow silica tubing, said mandrel having an annular space bounded by an inside surface;
   b. a helical continuous coil length of a second hollow silica tube located within the annular space of the mandrel and in fused contact with said inside surface at a multiplicity of points along the length of said helical coil;
   c. each portion of said coil having a direction generally transverse to the linear segment of said mandrel.

6. The rigid assembly of claim 5 where the mandrel has an outside diameter between about 3 and about 10 inches.

7. The rigid assembly of claim 5 where the continuous tubular coil has an inside diameter between about 0.05 and about 5 mm.

8. The rigid assembly of claim 5 further characterized by having a multiplicity of adjacent coils in fused contact with each other.

9. A rigid assembly of a hollow silica tube helically wound on a mandrel comprising:
   a. a mandrel of a substantially linear segment of a cylinder with a temperature coefficient of expansion within 10% of that of the silica over the temperature range −100° to about 800° C., said mandrel having at least one surface;
   b. a helical continuous coil length of a hollow silica tube located on a surface of said mandrel and in fused contact with said surface along at least a portion of the length of said helical coil;
   c. each portion of said coil having a direction generally transverse to the linear segment of said mandrel.

10. The rigid assembly of claim 9 where the mandrel is a hollow cylindrical segment with an outside surface and with an inside surface bounded by the annular space of the hollow segment.

11. The rigid assembly of claim 10 where the continuous tubular coil is located on the outside surface of the mandrel.

12. The rigid assembly of claim 11 further characterized in having a metallic film effective as a heating means deposited on a portion of the inside surface of said mandrel.

13. The rigid assembly of claim 11 further characterized in having heating means located within the annular space of said mandrel, at least a portion of said heating means contacting the inside surface of the mandrel.

14. The rigid assembly of claim 10 where the continuous tubular coil is located on the inside surface of the mandrel.

15. The rigid assembly of claim 14 further characterized in having a metallic film effective as a heating means deposited on a portion of the outside surface of said mandrel.

16. The rigid assembly of claim 9 where the mandrel is solid.

17. The rigid assembly of claim 9 where the mandrel is selected from the group consisting of fused silica and quartz.

18. The rigid assembly of claim 9 where the mandrel has an outside diameter between about 3 and about 10 inches.

19. The rigid assembly of claim 9 where the continuous tubular coil has an inside diameter between about 0.05 and about 5 mm.

20. The rigid assembly of claim 9 where the inner surface of the continuous tubular coil is coated with an organic stationary phase.

21. The rigid assembly of claim 9 where the inner surface of the continuous tubular coil is coated with an inorganic stationary phase.

* * * * *